(12) United States Patent
Erdler et al.

(10) Patent No.: US 9,664,633 B2
(45) Date of Patent: May 30, 2017

(54) RESISTIVE HYDROGEN SENSOR

(75) Inventors: Gilbert Erdler, Freiburg (DE); Holger Reinecke, Emmendingen (DE); Claas Müller, Freiburg (DE); Mirko Frank, Pfaffenweiler (DE)

(73) Assignee: Micronas GmbH, Freiburg, I. Br. (DE)

( * ) Notice: Subject to any disclaimer, the term of this patent is extended or adjusted under 35 U.S.C. 154(b) by 533 days.

(21) Appl. No.: 12/360,589

(22) Filed: Jan. 27, 2009

(65) Prior Publication Data

US 2009/0188316 A1     Jul. 30, 2009

(30) Foreign Application Priority Data

Jan. 28, 2008   (EP) ................................ 08001491

(51) Int. Cl.
| | |
|---|---|
| G01N 27/04 | (2006.01) |
| G01N 27/02 | (2006.01) |
| G01N 27/12 | (2006.01) |
| G01N 33/00 | (2006.01) |

(52) U.S. Cl.
CPC ........... *G01N 27/12* (2013.01); *G01N 33/005* (2013.01)

(58) Field of Classification Search
CPC .............................. G01N 27/12; G01N 33/005
USPC ............................................ 73/31.05; 422/94
See application file for complete search history.

(56) References Cited

U.S. PATENT DOCUMENTS

| 4,224,280 | A | * | 9/1980 | Takahama et al. ............. 422/98 |
| 4,953,387 | A | | 9/1990 | Johnson et al. |
| 7,041,591 | B1 | * | 5/2006 | Lee et al. ...................... 438/614 |
| 2004/0261500 | A1 | | 12/2004 | Ng et al. |
| 2005/0155858 | A1 | | 7/2005 | Monty et al. |
| 2005/0244701 | A1 | * | 11/2005 | Erdler et al. .................... 429/34 |
| 2007/0125153 | A1 | * | 6/2007 | Visel et al. ................... 73/31.05 |

FOREIGN PATENT DOCUMENTS

| DE | 102004011554 | 9/2005 |
| JP | 2003279522 | 10/2003 |

OTHER PUBLICATIONS

Reddy et al., Room temperature hydrogen sensor based on SnO2:La2O3, Hournal of the Electrochemical Society (2000) 147 (1) p. 390-393.*
Wang et al.: "Palladium-silver thin film for hydrogen sensing," Sensors and Actuators B, 2007, pp. 101-106, vol. 123.
Sakamoto et al: "Electrical resistance measurements as a function of composition of palladium—hydrogen (deuterium) systems by a gas phase method," J. Phys.: Condens. Matter, 1996, pp. 3399-3411, vol. 8.

* cited by examiner

*Primary Examiner* — Robert Eom
(74) *Attorney, Agent, or Firm* — Muncy, Geissler, Olds & Lowe, P.C.

(57) ABSTRACT

A resistive hydrogen sensor has at least two electrical connections and at least one resistance layer containing at least one suitable material for incorporating hydrogen, via which the electrical connections are connected to each other. The resistance layer adjoins at least one interface on a contact layer, which contains at least one chemical element from the fourth subgroup of the periodic table and/or carbon. The contact layer connected in series between the electrical connections to the resistance layer.

22 Claims, 6 Drawing Sheets

RESISTIVE HYDROGEN SENSOR

The invention relates to a resistive hydrogen sensor, which has at least two electrical connections and at least one resistance layer that alters its electrical resistance upon hydrogen absorption, wherein the electrical connections are connected to each other via the resistance layer.

Such a hydrogen sensor is disclosed in Sakamoto, Y. et al., "Electrical restistance [sic] measurements as a function of composition of palladium-hydrogen(deuterium) systems by a gas phase method", J. Phys.: Condens. Matter 8 (1996), pp. 3399-3411. As a resistance layer, the hydrogen sensor has a palladium film with a thickness of 50-60 μm, which is cut into ca. 2 mm×5 mm strips. The resistance layer is arranged in a stainless steel reaction vessel, which is connected via feed lines to a hydrogen and a deuterium reservoir. Nickel wires with a diameter of about 0.3 mm, which connect the resistance layer to electrical connections arranged on the outside of the reaction vessel, are welded onto the resistance layer. Electrical insulation for the nickel wires is provided by glass tubes, which are connected to the reaction vessel. The electrical resistance of the hydrogen-free palladium film is around 4.682±0.1067 mΩ at a temperature of 273 K. If the palladium film is exposed at room temperature to a hydrogen atmosphere with a pressure of one bar, its specific resistance changes by about 80% in comparison to a hydrogen-free palladium film. A disadvantage resides in the hydrogen sensor in that the electrical resistance of the palladium film is only relatively low, so that the resistance of the feed lines, which connect the connections to the palladium film, has a substantial effect on the measurement. Since the electrical resistance of the feed lines increases as the cross-section of the lines decreases, miniaturization of the hydrogen sensor is only possible to a limited extent. If the cross-section of the feed lines is made too small, the electrical resistance between the connections of the hydrogen sensor is then essentially defined solely by the feed lines. Temperature changes, which affect the electrical resistance of the palladium film and the feed lines, can also lead to measurement errors.

A hydrogen sensor of the aforesaid type is also disclosed in Wang, Min et al.: "Palladium-silver thin film for hydrogen sensing", Sensors and Actuators B 123 (2007), pp. 101-106, which has a resistance layer composed of a palladium-silver alloy, which is applied to a ceramic substrate via a thin film process. Compared to a resistance layer of pure palladium, the palladium-silver provides greater stability in the hydrogen incorporation. The resistance layer is configured with a meandering shape in order to increase electrical resistance. The disadvantage herein, however, resides in that the resistance layer covers a relatively large surface area on the substrate. In spite of the meandering configuration, the electrical resistance of the resistance layer is still relatively low in this hydrogen sensor as well.

The object is therefore to create a hydrogen sensor of the aforesaid type with compact dimensions that enables a high measuring sensitivity.

This object is achieved for the invention in that on at least one interface the resistance layer adjoins a contact layer, which contains at least one chemical element from the fourth subgroup of the periodic table and/or carbon, and in that the contact layer is connected in series between the electrical connections to the resistance layer.

In addition to the electrical resistance of the resistance layer, the contact resistance at the interface between the resistance layer and the contact layer also changes in an advantageous manner in response to a change in hydrogen concentration. This results in a marked change of the electrical resistance between the connectors of the hydrogen sensor and thus a greater measuring sensitivity. The hydrogen sensor can be manufactured via the process steps known to semiconductor manufacturing technology with compact dimensions by applying the resistance layer to a substrate, for example, a silicon substrate. Owing to the increased sensitivity compared to standard resistive hydrogen sensors, the resistance layer can be connected to the electrical connections via conductor paths with relatively small cross-sections. Preference is given to integration of the conductor paths on and/or in the substrate. The hydrogen sensor can thus be manufactured economically and with compact dimensions. The chemical element of the fourth subgroup of the periodic table, of which there is at least one, can be in particular hafnium or zirconium.

In a preferred embodiment of the invention, the contact layer is composed of titanium or contains titanium and/or a titanium-containing chemical compound. A particularly high measuring sensitivity can be achieved with such a contact layer. Furthermore, titanium is comparatively economical to obtain.

In an advantageous embodiment of the invention, the resistance layer is arranged on a substrate, wherein the contact layer of the resistance layer is covered, at least area-wise, so that at least a partial area of the resistance layer is arranged between the interface and the substrate. The sequence of layers comprising the resistance layer and the contact layer thus permits a relatively large interface between the resistance layer and the contact layer, even with low film thicknesses.

The contact layer is advantageously covered with a passivation layer. This prevents oxidation of the contact layer when the hydrogen sensor comes into contact with atmospheric oxygen.

Preference is given to the resistance layer being composed of palladium or having a palladium-containing alloy and/or a palladium-containing chemical compound. The hydrogen sensor then enables an even greater measuring sensitivity.

In another advantageous embodiment of the invention, the resistance layer contains a suitable chemical compound for incorporating hydrogen formed from a first chemical element A and a second chemical element B, which is of the type $AB_2$ or $AB_5$. With such a resistance layer it is also possible to achieve a high measuring sensitivity.

It is advantageous if the passivation layer is a metallic layer that adjoins a second interface on the resistance layer, and if the passivation layer is connected in series between the electrical connections to the contact layer and the resistance layer, and is preferably made of gold. With a current flow between the electrical connections, a voltage drop dependent on the hydrogen concentration in the resistance layer occurs on the first interface formed between the resistance layer and the contact layer and/or on the second interface formed between the contact layer and the passivation layer. The hydrogen sensor thus enables an even stronger measuring signal at the electrical connections.

In a preferred embodiment of the invention, the contact layer is configured as a thin film having a layer thickness of less than 300 μm, particularly less than 200 μm, and preferably less than 100 μm. The hydrogen sensor can then be economically produced by standard semiconductor manufacturing processes, for example, on a silicon substrate. The hydrogen sensor thus permits very compact dimensions.

In a possible embodiment of the invention, at least a partial area of the contact layer is arranged between the resistance layer and the substrate. The resistance layer thus also serves as passivation for the contact layer as well as a means for generating the measuring signal.

In a further embodiment of the invention, at least two of the layer arrays consisting in each case of at least the resistance layer, the adjoining contact layer, and where applicable the passivation layer adjoining the latter, are arranged on the substrate, wherein said layer arrays are connected in series between the electrical connections. The hydrogen sensor then enables an even stronger measuring signal, wherein the total measuring signal corresponds to the sum of the partial measuring signals generated on the individual layer arrays.

In a preferred embodiment of the invention, the resistance layer has at least one surface zone contacting the atmosphere, wherein preference is given to said surface zone laterally adjoining the interface situated between the resistance layer and the contact layer. The hydrogen sensor can then be used to detect gaseous hydrogen in the environment. By continuous measuring of the electrical resistance between the connections of the hydrogen sensor, the partial pressure of the hydrogen in the environment can be distinctly determined. If the surface zone in contact with the atmosphere is adjacent to the interface, the hydrogen can reach the interface from the surface zone via short diffusion paths. The measuring signal of the hydrogen sensor then reacts quickly to changes in the hydrogen partial pressure.

In another advantageous embodiment of the invention, the resistance layer is a hydrogen storage unit connected to a fuel cell and the electrical connections are connected to an evaluator, which is configured as a charge level indicator for the hydrogen storage unit. Preference is given to the evaluator having a display for charge level. This permits easy checking of the charge level of the hydrogen storage unit and/or easy measurement of the volume of hydrogen incorporated in the hydrogen storage unit.

It is advantageous if the fuel cell has a layer stack consisting of at least two electrode layers and an membrane layer situated between them, and if the resistance layer is arranged, at least area-wise, between said layer stack and the substrate. This results in a highly compact arrangement in which the fuel cell is arranged on the hydrogen sensor, thus conserving chip surface area. The membrane layer is an ion-conducting layer, preferably a polymer-electrolyte membrane.

Illustrative embodiments of the invention are explained in more detail in the following, wherein.

Figure 1:
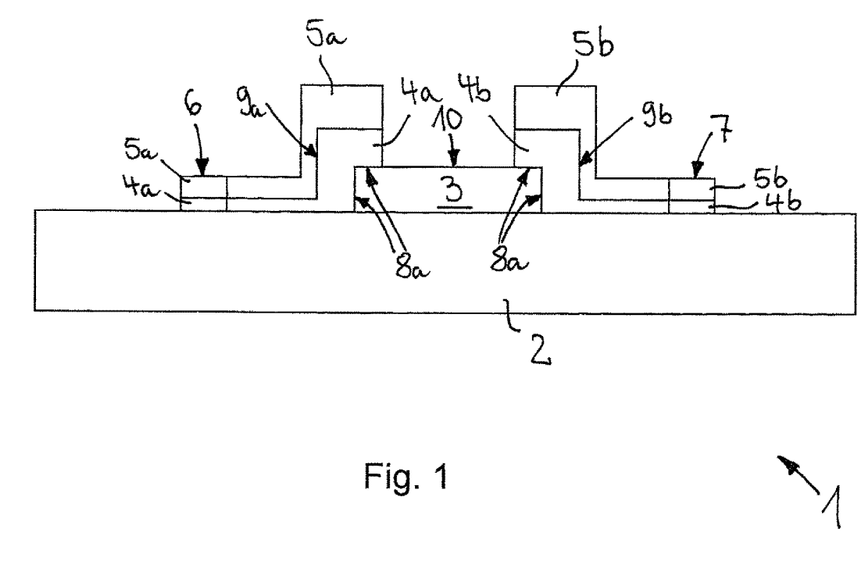
FIG. 1 shows a cross-section through a first illustrative embodiment of a hydrogen sensor.

A resistive hydrogen sensor designated in entirety by 1 in FIG. 1 has a substrate 2, on which are arranged a resistance layer 3 composed of palladium or a palladium alloy, two electrical contact layers 4a, 4b composed of titanium, and two passivation layers 5a, 5b.

The passivation layers 5a, 5b are composed of an electrically conductive material, preferably a noble metal, particularly gold and in each case they have a partial area serving as an electrical connection 6, 7. A current source for an evaluator (not shown in any greater detail in the drawing) is connected to the connectors 6, 7. The substrate can be an electrically conductive substrate with passivation layers, a semiconductor substrate, such as, e.g., a silicon substrate, or an electrically insulating substrate, for example a ceramic substrate or a plastic substrate.

In each case each contact layer 4a, 4b adjoins a first interface 8a, 8b on the resistance layer 3 and a second interface 9a, 9b separated therefrom on the passivation layer 5a, 5b. The passivation layers 5a, 5b, the contact layers 4a, 4b, and the resistance layer 3 are connected in series between the connections 6, 7 in such a way that an electric current flowing between the connections 6, 7 permeates the first interfaces 8a, 8b and the second interfaces 9a, 9b.

Figure 2:
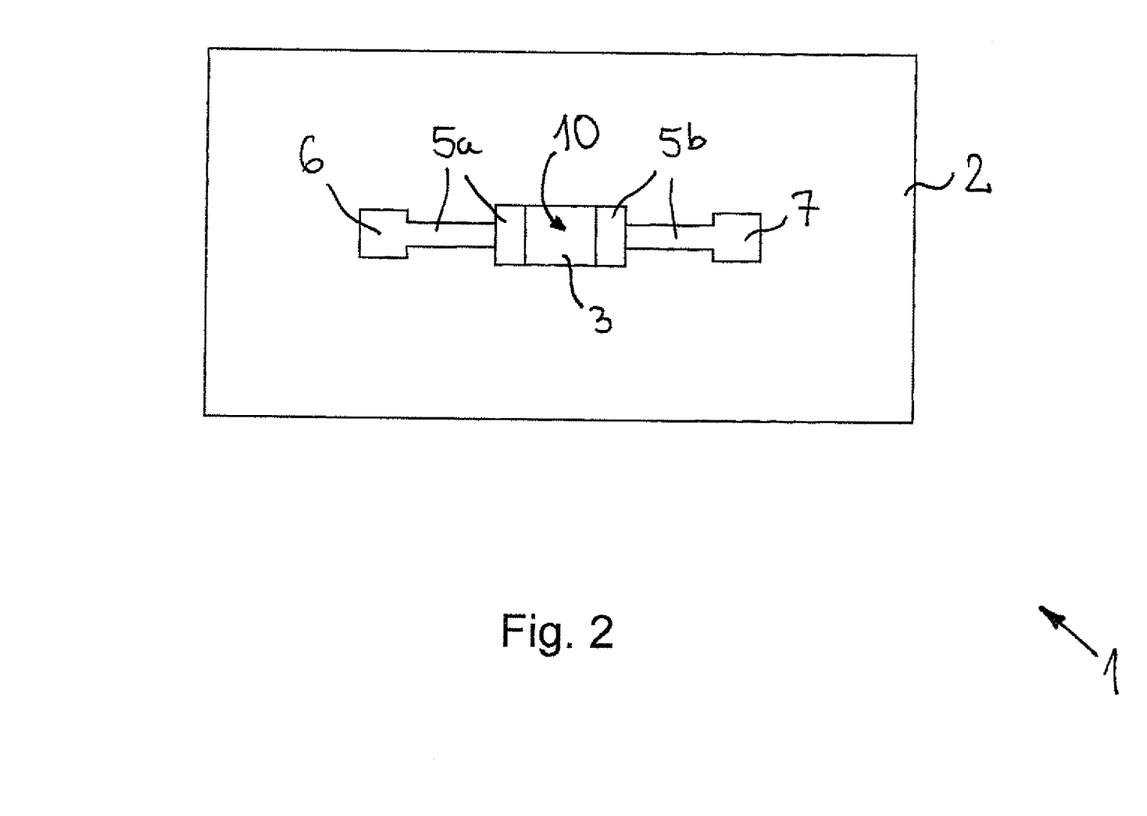
FIG. 2 shows a view from above of the hydrogen sensor shown in FIG. 1.

It can be discerned in FIGS. 1 and 2 that the interfaces 8a, 8b are arranged on border areas of the resistance layer 3 separated from each other, and that the contact layers 4a, 4b in each case cover one of these border areas with a partial area. Another partial area of each contact layer 4a, 4b is in each case directly arranged on the substrate 2. Between the partial area covering the resistance layer 3 and the partial area adjoining the substrate 2, the contact layers 4a, 4b in each case have a step-like or ledge-like outline.

The passivation layer 5a, 5b covers its allocated contact layer 4a, 4b completely in each case. The passivation layer 5a, 5b thus conforms to the step-like or ledge-like outline of the underlying contact layer 4a, 4b. The passivation layer 5a, 5b and the contact layer 4a, 4b are in each case configured as thin films. The film thickness of the passivation layer 5a, 5b and the contact layer 4a, 4b can be, for example, around 100 μm.

It can also be discerned in FIG. 2 that the passivation layer 5a, 5b and the contact layer 4a, 4b in each case have a greater width at the connections 6, 7 and the partial area covering the resistance layer 3 than in a section situated between the connections 6, 7 and the partial area covering the resistance layer 3.

Between the contact layers 4a, 4b, the resistance layer 3 has a surface zone 10 contacting the atmosphere. This surface zone 10 laterally adjoins the first interface 8a, 8b situated between the resistance layer 3 and the respective contact layer 4a, 4b.

Figure 3:
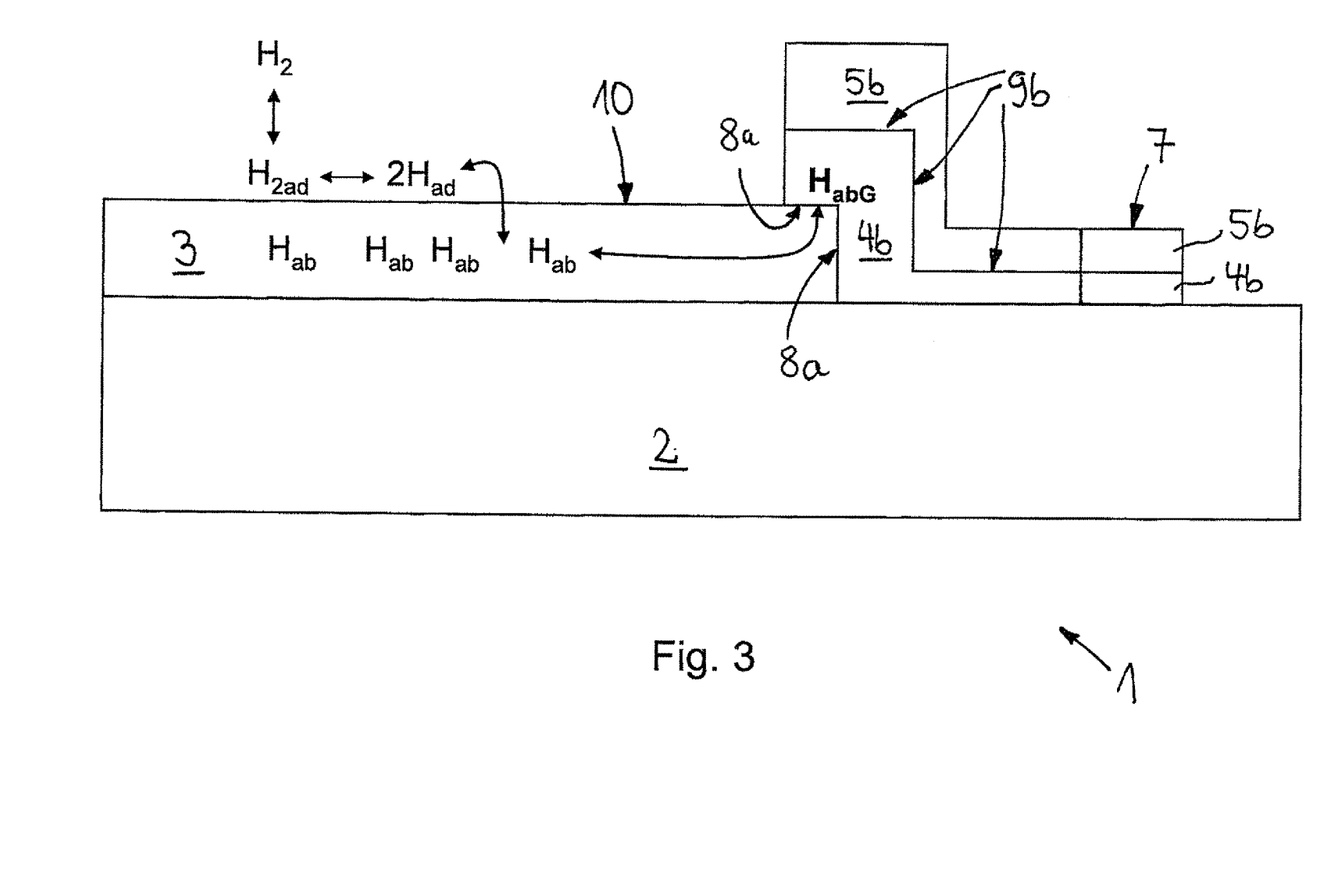
FIG. 3 is a diagrammatic illustration showing adsorption of hydrogen on the surface of a palladium film and absorption of hydrogen by the palladium film of the hydrogen gas sensor.

It can be discerned in FIG. 3 that the gaseous hydrogen molecules $H_2$ located in the vicinity of the surface zone 10 can be adsorbed on the surface zone 10 in the form of hydrogen atoms $H_{ad}$. The hydrogen atoms $H_{ad}$ are absorbed by the resistance layer 3 and incorporate themselves in the latter. In the resistance layer 3 the absorbed hydrogen atoms $H_{ab}$ diffuse to the first interfaces 8a, 8b and where applicable to the second interfaces 9a, 9b.

Figure 4:
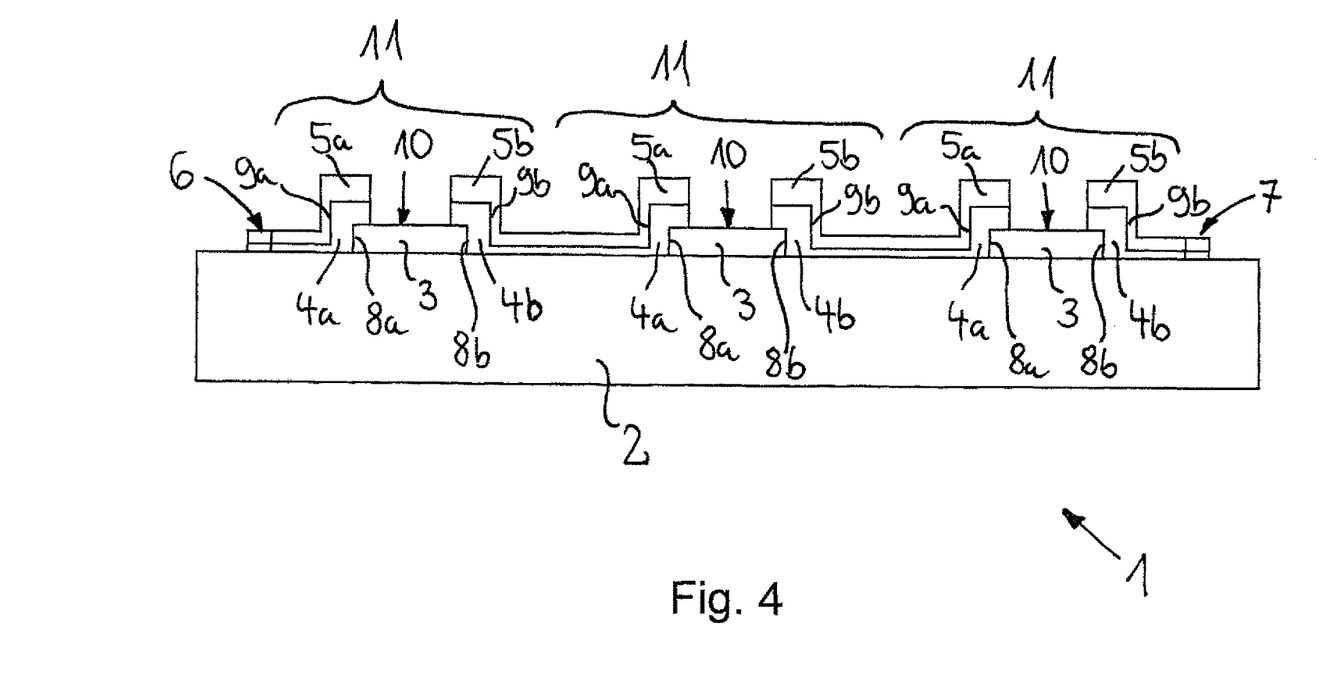
FIG. 4 shows a cross-section through a second illustrative embodiment of the hydrogen sensor.
Figure 5:
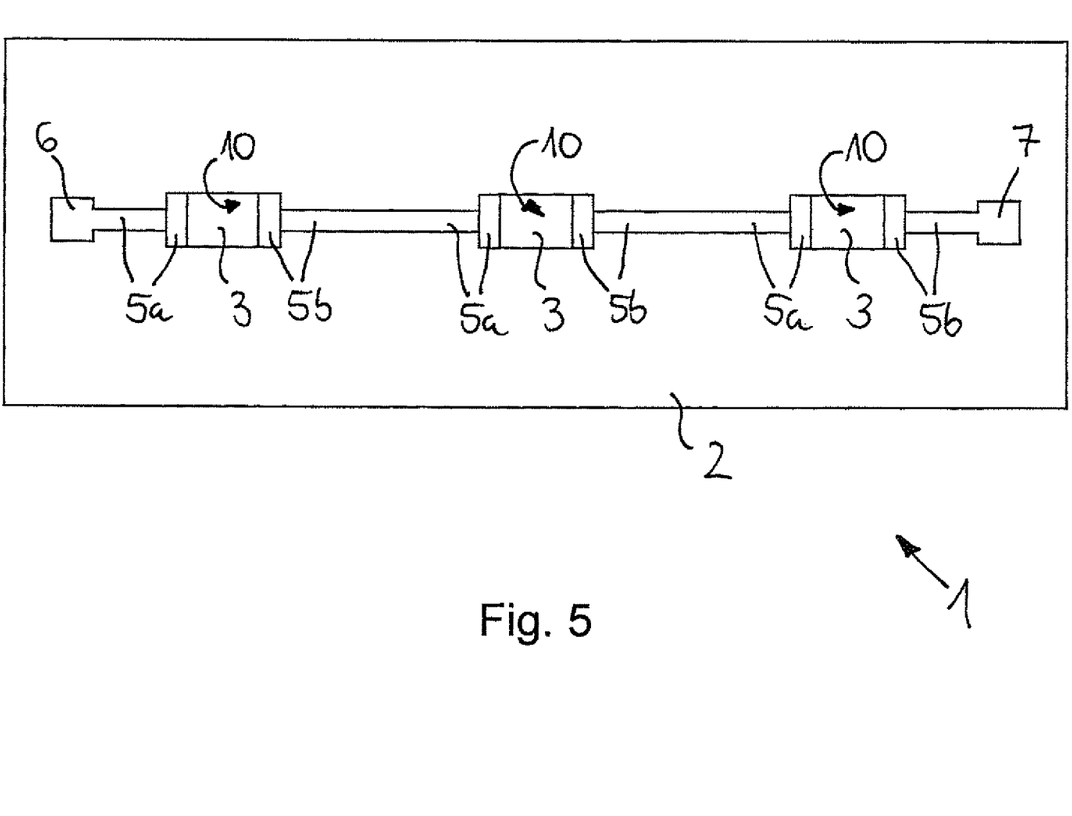
FIG. 5 shows a view from above of the hydrogen sensor shown in FIG. 4.

In the illustrative embodiment shown in FIGS. 4 and 5, a plurality of layer arrays 11 is arranged on the substrate 2, said arrays in each case comprising the resistance layer 3, the contact layer 4a, 4b adjoining it on the first interface 8a, 8b, and the passivation layer 5a, 5b adjoining the contact layer 4a, 4b on the second interface 9a, 9b. It can be clearly discerned that these layer arrays 11 are connected in series between the connections 6, 7 in such a way that the electric current applied to the connections 6, 7 by the current source flows through all first interfaces 8a, 8b and through at least two of the second interfaces 9a, 9b.

Figure 6:
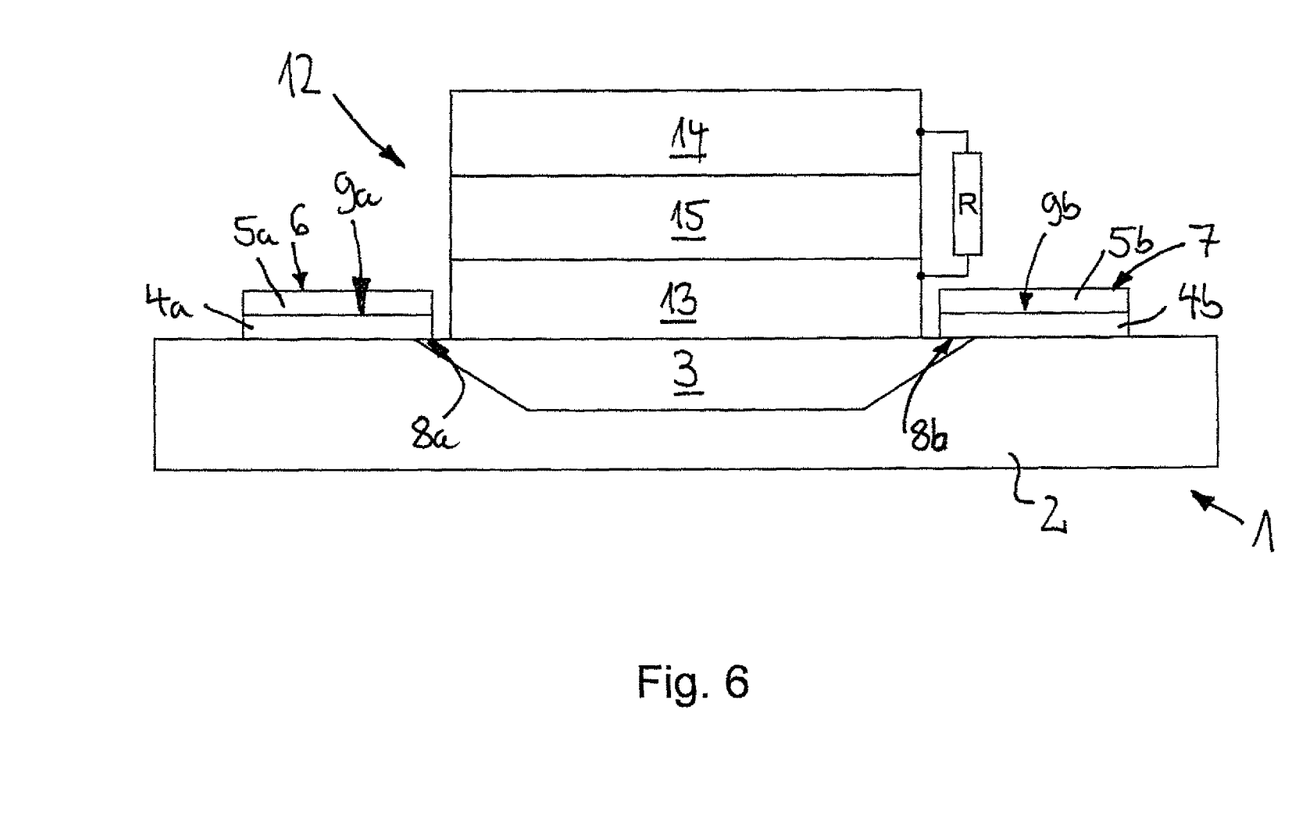
FIG. 6 shows a cross-section through a third embodiment of the hydrogen sensor integrated in a fuel cell, wherein an electrical consumer connected to the fuel cell is schematically represented by a resistance symbol.

In the illustrative embodiment shown in FIG. 6, the resistance layer is configured as a thick film, which serves as a hydrogen storage unit for a fuel cell 12. The electrical connections 6, 7 are connected to an evaluator, which is not shown in any greater detail in the drawing and which is configured as a charge level indicator for the hydrogen storage unit. The evaluator can be integrated in the substrate 2 as an electronic circuit.

The fuel cell is configured as a layer stack, which has two electrode layers 13, 14 and a membrane layer 15 situated between them. A first electrode layer 13 acts as a cathode and a second electrode layer 14 in contact with an oxygen-containing atmosphere acts as an anode. The membrane layer 15 is configured as a polymer-electrolyte membrane. The layer stack is arranged on the resistance layer 3 between the first interfaces 8a, 8b. Between the electrode layers 13, 14 there is an electric voltage which can be measured.

The invention claimed is:

1. A resistive hydrogen sensor comprising:
a substrate;
at least two electrical connections;
a single palladium resistance layer, which changes its electrical resistance with hydrogen uptake, disposed on the substrate;
left side and right side contact layers disposed above the palladium resistance layer and to each side of the palladium resistance layer; and
a gold passivation layer disposed above the left side and right side contact layers,
wherein said at least two electrical connections are connected to each other via a layer array, including the palladium resistance layer,
wherein the palladium resistance layer adjoins, at each of two first interfaces, the left side and right side contact layers,
wherein each of the left side and right side contact layers contain at least one chemical element from the fourth subgroup of the periodic table and/or carbon,
wherein the left side and right side contact layers are electrically connected in series between the at least two electrical connections through the palladium resistance layer,
wherein a portion of the left side and right side contact layers and a portion on the palladium resistance layer are arranged on the substrate,
wherein the gold passivation layer is disposed above the left side and right side contact layers such that the gold passivation layer does not directly contact the palladium resistance layer,
wherein a lower surface of the palladium resistance layer directly contacts the substrate and an upper surface of the palladium resistance layer directly contacts atmospheric oxygen, and
wherein the left side and right side contact layers are each formed of only a single layer and directly contact the substrate on a lower surface thereof and directly contact one of the at least two electrical connections and the gold passivation layer on an upper surface thereof, respectively.

2. The resistive hydrogen sensor as in claim 1, wherein the left side and right side contact layers are each composed of titanium or contains titanium and/or a titanium-containing chemical compound.

3. The resistive hydrogen sensor as in claim 1, wherein, the palladium resistance layer is arranged on the substrate, and wherein the left side and right side contact layers, at least area-wise, cover the palladium resistance layer in such a way that at least a partial area of the palladium resistance layer is arranged between the two first interfaces and the substrate.

4. The resistive hydrogen sensor as in claim 1, wherein the palladium resistance layer contains a suitable chemical compound for incorporating hydrogen formed from a first chemical element A and a second chemical element B.

5. The resistive hydrogen sensor as in claim 1, wherein the gold passivation layer is a metallic film, which adjoins the palladium resistance layer at a second interface, and wherein the gold passivation layer is connected in series between the at least two electrical connections to the left side and right side contact layers and the palladium resistance layer.

6. The resistive hydrogen sensor as in claim 1, wherein each of the left side and right side contact layers is configured as a thin film having a film thickness of less than 300 µm.

7. The resistive hydrogen sensor as in claim 1, wherein at least a partial area of the left side and right side contact layers is arranged between the palladium resistance layer and the substrate.

8. The resistive hydrogen sensor as in claim 1, further including, on the substrate, at least two of the layer array connected in series between the at least two electrical connections.

9. The resistive hydrogen sensor as in claim 1, wherein the palladium resistance layer has at least one surface zone contacting the atmosphere, and wherein said at least one surface zone laterally adjoins the two first interfaces.

10. The resistive hydrogen sensor as in claim 1, wherein the palladium resistance layer is a hydrogen storage unit connected to a fuel cell and wherein the at least two electrical connections are connected to an evaluator which is configured as a charge level indicator for the hydrogen storage unit.

11. The resistive hydrogen sensor as in claim 10, wherein the fuel cell has a layer stack consisting of at least two electrode layers and a membrane layer situated between them, and wherein the palladium resistance layer is, at least area-wise, arranged between said layer stack and the substrate.

12. The resistive hydrogen sensor according to claim 1, wherein each of the left side and right side contact layers is configured as a thin film having a film thickness of less than 200 µm.

13. The resistive hydrogen sensor according to claim 1, wherein each of the left side and right side contact layers is configured as a thin film having a film thickness of less than 100 µm.

14. The resistive hydrogen sensor as in claim 1,
wherein the at least two electrical connections are connected to the gold passivation layer and the left side and right side contact layers, and
wherein the gold passivation layer and the left side and right side contact layers have a greater width at a first end that is connected to the at least two electrical connections and a second end covering the palladium resistance layer than in a section situated between the first end and the second end in a plan view.

15. A resistive hydrogen sensor formed on a substrate, the sensor comprising:
two electrical connections;
a single palladium resistance layer disposed on the substrate that changes its electrical resistance with hydrogen uptake;
left side and right side contact layers disposed above the palladium resistance layer; and a gold passivation layer disposed above the left side and right side contact layers, wherein the two electrical connections are connected to each other via the palladium resistance layer, wherein the palladium resistance layer adjoins the left side and right side contact layers, each of said left side and right side contact layers containing at least one chemical element from the fourth subgroup of the periodic table and/or carbon, wherein the left side and right side contact layers are electrically connected in series between the electrical connections through the palladium resistance layer, wherein the gold passivation layer is disposed above the left side and right side contact layers such that the gold passivation layer does not directly contact the palladium resistance layer, wherein a lower surface of the palladium resistance layer directly contacts the substrate and an upper surface of the palladium resistance layer directly contacts atmospheric oxygen, and wherein the left side and right side contact layers are each formed of only a single layer and directly contact the substrate on a lower surface thereof and directly contact one of the two electrical connections and the gold passivation layer on an upper surface thereof, respectively.

16. The resistive hydrogen sensor as in claim 15, wherein the two electrical connections are connected to the gold passivation layer and the left side and right side contact layers, and wherein the gold passivation layer and the left side and right side contact layers have a greater width at a first end that is connected to the two electrical connections and a second end covering the palladium resistance layer than in a section situated between the first end and the second end in a plan view.

17. A resistive hydrogen sensor, comprising:
a substrate;
two electrical connections;
a single palladium resistance layer disposed on the substrate and disposed between and connecting the two electrical connections;
a contact layer disposed on each end of the palladium resistance layer, the contact layer comprising a chemical element from the fourth subgroup of the periodic table; and
a gold passivation layer disposed on the contact layer,
wherein the gold passivation layer is insulated from the palladium resistance layer such that the gold passivation layer does not directly contact the palladium resistance layer, wherein a lower surface of the palladium resistance layer directly contacts the substrate and an upper surface of the palladium resistance layer directly contacts atmospheric oxygen, and wherein the contact layer disposed on each end of the palladium resistance layer are each formed of only a single layer and directly contact the substrate on a lower surface thereof and directly contact one of the two electrical connections and the gold passivation layer on an upper surface thereof, respectively.

18. The resistive hydrogen sensor according to claim 17, wherein the contact layer is composed of titanium.

19. The resistive hydrogen sensor as in claim 17, wherein the two electrical connections are connected to the gold passivation layer and the contact layer, and wherein the gold passivation layer and the contact layer have a greater width at a first end that is connected to the two electrical connections and a second end covering the palladium resistance layer than in a section situated between the first end and the second end in a plan view.

20. A resistive hydrogen sensor, comprising:
a substrate;
two electrical connections;
a single palladium resistance layer disposed on the substrate and disposed between and connecting the two electrical connections;
a contact layer disposed on each end of the palladium resistance layer, the contact layer comprising a chemical element from the fourth subgroup of the periodic table; and
a gold passivation layer disposed on the contact layer,
wherein the contact layer covers only each end of the palladium resistance layer and does not extend across an entirety of the palladium resistance layer, wherein a lower surface of the palladium resistance layer directly contacts the substrate and an upper surface of the palladium resistance layer directly contacts atmospheric oxygen, and wherein the contact layer disposed on each end of the palladium resistance layer are each formed of only a single layer and directly contact the substrate on a lower surface thereof and directly contact one of the two electrical connections and the gold passivation layer on an upper surface thereof, respectively.

21. The resistive hydrogen sensor according to claim 20, wherein the contact layer is composed of titanium.

22. The resistive hydrogen sensor as in claim 20, wherein the two electrical connections are connected to the gold passivation layer and the contact layer, and wherein the gold passivation layer and the contact layer have a greater width at a first end that is connected to the two electrical connections and a second end covering the palladium resistance layer than in a section situated between the first end and the second end in a plan view.

* * * * *

UNITED STATES PATENT AND TRADEMARK OFFICE
CERTIFICATE OF CORRECTION

PATENT NO. : 9,664,633 B2
APPLICATION NO. : 12/360589
DATED : May 30, 2017
INVENTOR(S) : Erdler Page 1 of 1

It is certified that error appears in the above-identified patent and that said Letters Patent is hereby corrected as shown below:

On the Title Page (73) Assignee shows:
Micronas GmbH, Freiburg, I. Br. (DE)
(73) Assignee should show:
TDK-Micronas GmbH, Freiburg, I. Br. (DE)

Signed and Sealed this
Seventh Day of August, 2018

Andrei Iancu
*Director of the United States Patent and Trademark Office*